United States Patent
Fox et al.

(10) Patent No.: US 8,061,298 B2
(45) Date of Patent: *Nov. 22, 2011

(54) STENT MANDREL FIXTURE AND METHOD FOR SELECTIVELY COATING SURFACES OF A STENT

(75) Inventors: Jason Fox, Menlo Park, CA (US); Nathan Harold, San Jose, CA (US); Barry Templin, Milpitas, CA (US); Andrew Tochterman, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,471

(22) Filed: Mar. 10, 2010

(65) Prior Publication Data

US 2010/0162950 A1    Jul. 1, 2010

Related U.S. Application Data

(60) Continuation of application No. 11/654,413, filed on Jan. 16, 2007, which is a division of application No. 10/676,545, filed on Sep. 30, 2003, now Pat. No. 7,198,675.

(51) Int. Cl.
*B05C 13/02* (2006.01)

(52) U.S. Cl. ........ 118/500; 118/504; 118/505; 623/1.46; 623/1.47; 623/1.48

(58) Field of Classification Search ............... 118/500, 118/504, 505; 623/1.46–1.48, 1.1
See application file for complete search history.

(56) References Cited

U.S. PATENT DOCUMENTS

| | | |
|---|---|---|
| 4,529,792 A | 7/1985 | Barrows |
| 4,762,128 A | 8/1988 | Rosenbluth |
| 5,037,392 A | 8/1991 | Hillstead |
| 5,363,881 A | 11/1994 | Larkin |
| 5,578,048 A | 11/1996 | Pasqualucci et al. |
| 5,879,499 A * | 3/1999 | Corvi .................. 156/175 |
| 6,270,504 B1 | 8/2001 | Lorentzen et al. |
| 6,575,933 B1 | 6/2003 | Wittenberger et al. |
| 7,011,675 B2 | 3/2006 | Hemerick et al. |
| 7,604,700 B2 * | 10/2009 | Fox et al. .............. 118/500 |
| 2003/0083646 A1 | 5/2003 | Sirhan et al. |
| 2003/0215564 A1* | 11/2003 | Heller et al. ........... 427/2.25 |
| 2004/0213893 A1 | 10/2004 | Boulais |
| 2004/0260379 A1 | 12/2004 | Jagger et al. |

* cited by examiner

*Primary Examiner* — Laura Edwards
(74) *Attorney, Agent, or Firm* — Squire, Sanders & Dempsey (US) LLP

(57) ABSTRACT

A stent mandrel fixture for supporting a stent during the application of a coating substance is provided. A method supporting a stent during the application of a coating substance is also provided.

11 Claims, 4 Drawing Sheets

Unexpanded

Expanded

Unexpanded

Expanded

Unexpanded

Expanded

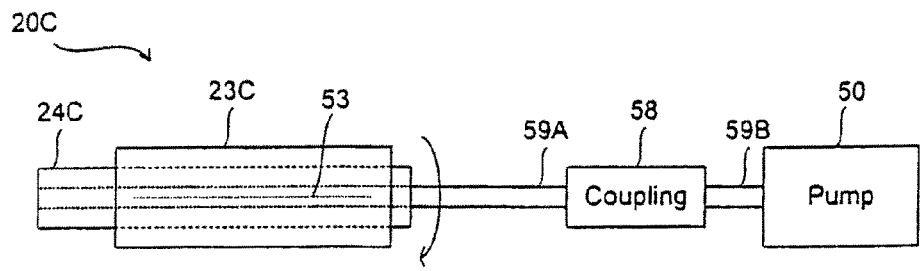
FIG. 3D
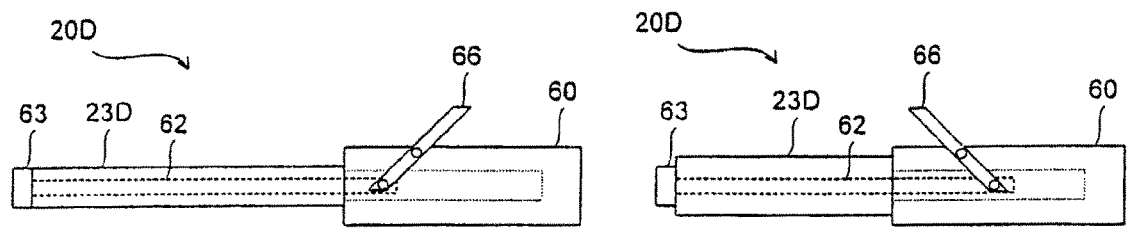
Unexpanded
FIG. 4A
Expanded
FIG. 4B
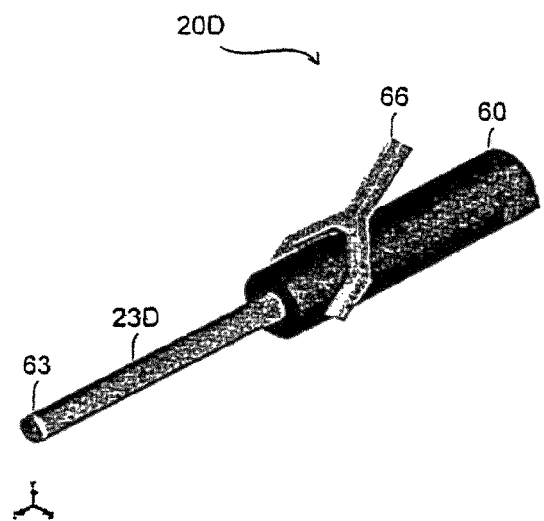
FIG. 4C Unexpanded Expanded

STENT MANDREL FIXTURE AND METHOD FOR SELECTIVELY COATING SURFACES OF A STENT

This is a continuation application of U.S. Ser. No. 11/654,413 which was filed Jan. 16, 2007, and which is a divisional of U.S. Ser. No. 10/676,545, which was filed on Sep. 30, 2003, now U.S. Pat. No. 7,198,675, issued on Apr. 3, 2007, both of which are incorporated herein by reference. U.S. Pat. No. 7,604,700, issued Oct. 20, 2009, is a continuation application of U.S. Ser. No. 10/676,545 and is related to this application.

TECHNICAL FIELD

This invention relates generally to stent mandrel fixtures, and more particularly, but not exclusively, provides a stent mandrel fixture and method for coating an outer surface of a stent.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is that both the inner surface and an outer surface of the stent are coated with the same therapeutic substance. Accordingly, the therapeutic substance will be dispensed locally by being absorbed by the vessel wall from the outer surface of the stent and will be dispensed downstream as blood carries the therapeutic substance from the inner surface. In some circumstances there may be a need of only having the outer surface of the stent coated with the therapeutic substance. Alternatively, there may be a need of coating the outer surface of the stent with a first type of a drug and the inner surface with a second type of a drug. For example, the stent's outer surface could be coated with an anti-inflammatory drug or anti-restenosis drug to treat inflammation or hyper-migration and proliferation of vascular smooth muscle cells, respectively. The stent's inner wall could be coating with an anti-coagulant to reduce platelet aggregation, clotting and thrombus formation.

Accordingly, a new stent mandrel fixture and method are needed to overcome this shortcoming.

SUMMARY

In accordance with one embodiment of the invention, a stent mandrel fixture is provided, comprising a masking element configured to be inserted through a bore of a stent, the masking element having an expanded configuration and a retracted configuration and an expansion causing mechanism capable of expanding the masking element from the retracted configuration to the expanded configuration to cause the masking element to make contact with and mask an inner surface of the stent.

In accordance with another embodiment of the invention, a fixture to support a stent during the application of a coating composition to the stent is provided, comprising a hollow tubular member configured to be inserted into a longitudinal bore of a stent; a rod extending through the tubular member; and a mechanism to cause the tubular member to expand and retract to support the stent during the application of a coating composition to the stent.

In accordance with another embodiment of the invention, a fixture to support a stent during the application of a coating composition to the stent is provided, comprising a mandrel base; a rod extending out from the mandrel base, the rod configured to be moved in and out of the mandrel base; and a support element integrated with the rod, the support element having a first position of being engaged with the stent and a second position of being disengaged from the stent, wherein the movement of the rod in and out of the mandrel base causes the engagement and disengagement of the support element with the stent. A lever can be used to drive the rod in and out of the mandrel base.

In accordance with other embodiments of the invention, methods of coating a stent with a composition are provided, comprising: positioning a stent on a fixture of the invention; and applying a coating composition to the stent.

In accordance with yet another embodiment, a method of coating a stent with a composition is provided, comprising inserting a tubular member inside a longitudinal bore of a stent, the stent comprising struts separated by gaps; expanding the tubular member such that the tubular member at least partially extends through the gaps; and applying a coating composition to the stent.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 3D illustrates a stent mandrel fixture in accordance with another embodiment of the invention;

FIG. 4A, FIG. 4B, FIG. 4C, and FIG. 4D illustrate a stent mandrel fixture in accordance with another embodiment of the invention;

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
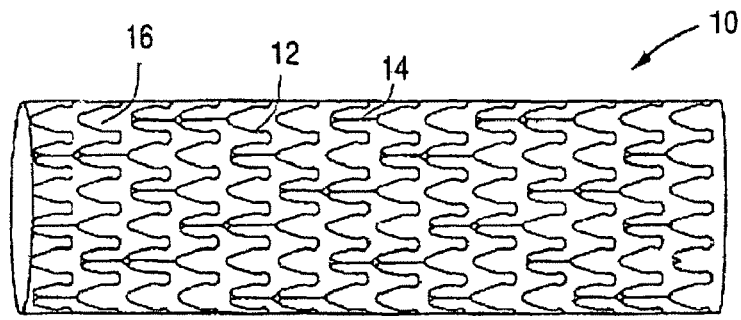
FIG. 1 illustrates a conventional stent.
Figure 2A:
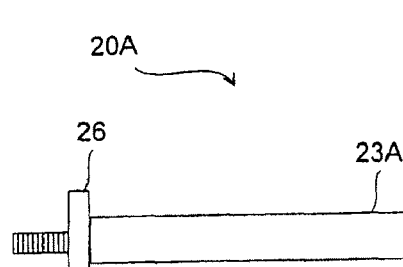
FIG. 2A and FIG. 2B illustrate a stent mandrel fixture in accordance with an embodiment of the invention.
Figure 2B:
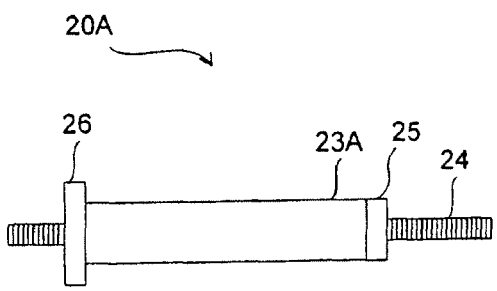

FIG. 2A and FIG. 2B illustrate a stent mandrel fixture 20A in accordance with an embodiment of the invention. The fixture 20A for supporting the stent 10 includes a bladder or expandable or elastic tube 23A, a threaded rod 24, a nut 25, and a lock member 26. The stent mandrel fixture 20A can be coupled to engines (not shown) to provide rotational and lateral motion to a mounted stent 10 during a coating process.

The threaded rod 24 passes through an inner bore of the tube 23A, lock member 26, and nut 25. The tube 23A is fixed at one end to the lock member 26 while the nut is rotationally mounted on the rod 24. In an alternative embodiment, the lock member 26 can also be rotationally mounted to the rod 24 (and therefore not fixed to the tube 23A) thereby enabling the adjustable positioning of the lock member 26. While the lock member 26 as shown has an outer diameter greater than the outer diameter of the nut 25, it will be appreciated by one of ordinary skill in the art that the lock member 26 can have an outer diameter less than, substantially equal to, or greater than the outer diameter of the nut 25. The outer diameter of the lock member 26 must only be at least equal to the outer diameter of the stent 10 so that the stent 10 does not slide past the lock member 26.

The nut 25 is an expansion causing mechanism. Rotation of the nut 25, such that the nut 25 presses against the tube 23A, causes the tube 23A to compress in a lateral direction against the lock member 26 while expanding radially outwards from the rod 24 as shown in FIG. 2B and FIG. 5B. Rotation of the nut 25 away from the tube 23A causes the tube 23A to return back to its uncompressed or natural state as shown in FIG. 2A and FIG. 5A.

It will be appreciated by one of ordinary skill in the art that the nut 25 can be electrically driven or otherwise tightened without human intervention in order to automate the process of coating a stent 10, thereby increasing throughput. Additionally, with the use of the nut 25, incremental rotation of the nut 25 can allow for the bladder or tube 23A to be expanded in an incremental fashion.

The tube 23A can be made of or coated with a non-stick substance, such as TEFLON. In one embodiment, the tube 23A, when compressed laterally, has a length equal to at least the length of the stent 10, thereby enabling masking of the entire length of the inner diameter of the stent 10. In another embodiment, the tube 23A, when compressed laterally, has a length shorter than the length of the stent 10, thereby supporting the stent 10 with minimal contact with the stent 10. In an unexpanded state (i.e., not compressed laterally), the tube 23A has an outer diameter smaller than the inner diameter of the stent 10 (as positioned on the tube 23A). When the tube 23A expands (i.e., is compressed laterally), the outer diameter of the tube 23A expands to at least the inner diameter of the stent 10, thereby acting to hold the stent 10 in place and to mask at least a portion of the inner surface of the stent 10. The masking of the inner surface of the stent 10 prevents the inner surface from being coated with a composition during a coating process. Accordingly, when the tube 23A is in an expanded state, only the outer surface and sidewalls of the stent 10 are coated with the composition from a spray flow, which is discharged from a nozzle assembly (not shown). In other embodiments of the invention to be discussed further below in conjunction with FIG. 6A to 6D, the tube 23A can be further radially expanded to enable masking of the sidewalls in addition to the inner surface of the stent 10.

Figure 5A:
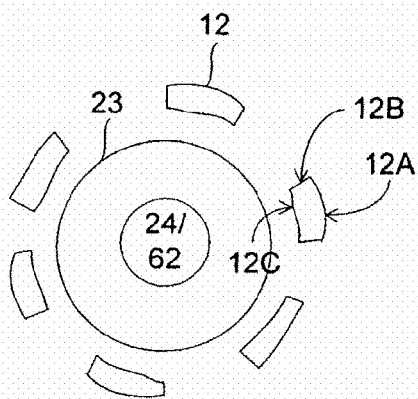
FIG. 5A and FIG. 5B illustrate cross sections of a stent mandrel fixture according to an embodiment of the invention.
Figure 5B:
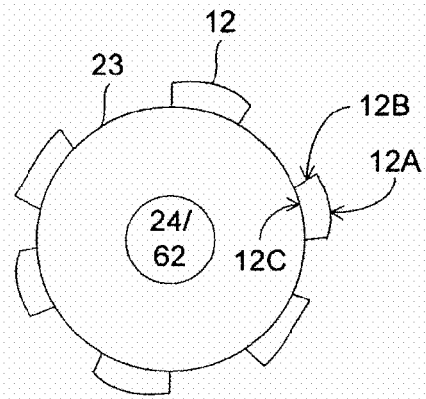
Figure 6A:
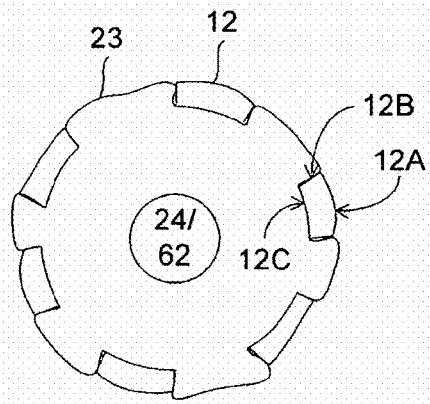
FIG. 6A illustrates a cross section of a stent mandrel fixture according to an embodiment of the invention.
Figure 6B:
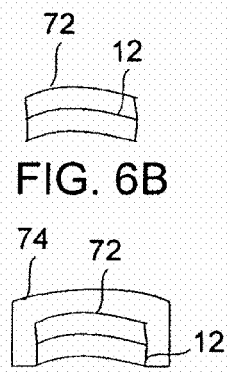
FIG. 6B-6D illustrate cross sections of a stent strut after coating on the stent mandrel fixture of FIG. 2, FIG. 3, or FIG. 4.
Figure 6C:
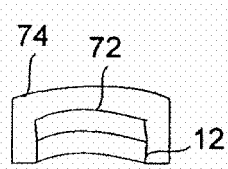
Figure 6D:
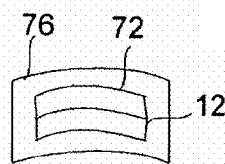

During operation of the stent mandrel fixture 20A, a stent 10 is loaded onto the fixture by first removing the nut 25 and then placing the stent 10 over the tube 23A when tube 23A is in an uncompressed state, as shown in FIG. 5A. The nut 25 is then loaded onto the rod 24 and tightened against the tube 23A, causing the tube 23A to compress laterally and expand radially outwards from the rod 24, as shown in FIG. 5B. In one embodiment of the invention, the tube 23A can expand radially outwards to substantially mask the inner surface of the stent 10, as shown in FIG. 5B. In another embodiment of the invention, the tube 23A can comprise a flexible and/or thin material, such as latex, and expands radially outwards to substantially mask the inner surface of the stent 10 as well as the sidewalls of the stent 10, as shown in FIG. 6A. In other words, the tube 23A is capable of protruding at least partially through the gaps 16 between the stent struts 12 to mask the sidewalls of the stent struts 12.

After the tube 23A is expanded radially outwards, a spray nozzle (not shown) sprays a composition onto the stent 10. As the inner diameter of the stent 10 is masked, only the sidewalls and outer surface of the stent 10 are coated with a composition. In another embodiment of the invention, the sidewalls can also be masked and accordingly, only the outer surface of the stent 10 is coated with the composition.

After the coating of the stent 10, the nut 25 is loosened, thereby enabling the tube 23A to return to a non-expanded state and further enabling removal of the stent 10 from the stent mandrel fixture 20A. The stent 10 can then have the inner surface coated via electroplating or spray coating. Without masking the outer surface of the stent 10, both electroplating and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner surface and the outer surface of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The components of the coating substance or composition can include a solvent or a solvent system comprising multiple solvents, a polymer or a combination of polymers, a therapeutic substance or a drug or a combination of drugs. Representative examples of polymers that can be used to coat a stent or medical device include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerolsebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can include any substance capable of exerting a therapeutic or prophylactic effect. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 3A:
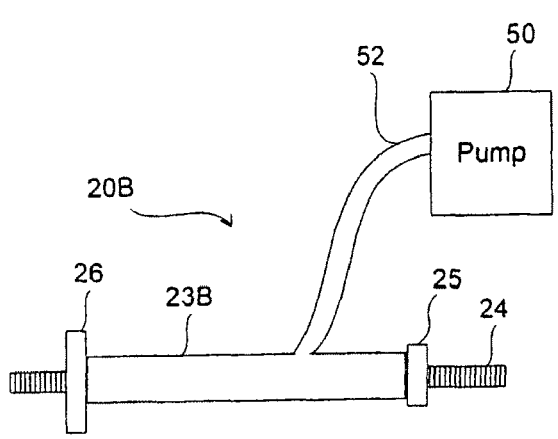
FIG. 3A, FIG. 3B, and FIG. 3C illustrate a stent mandrel fixture in accordance with another embodiment of the invention.
Figure 3B:
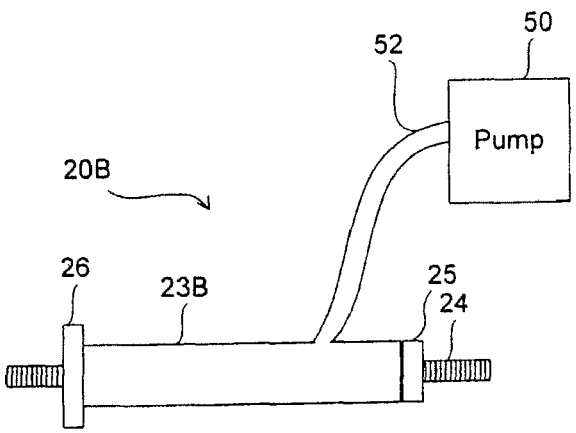
Figure 3C:
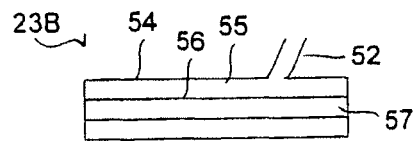
Figure 4D:
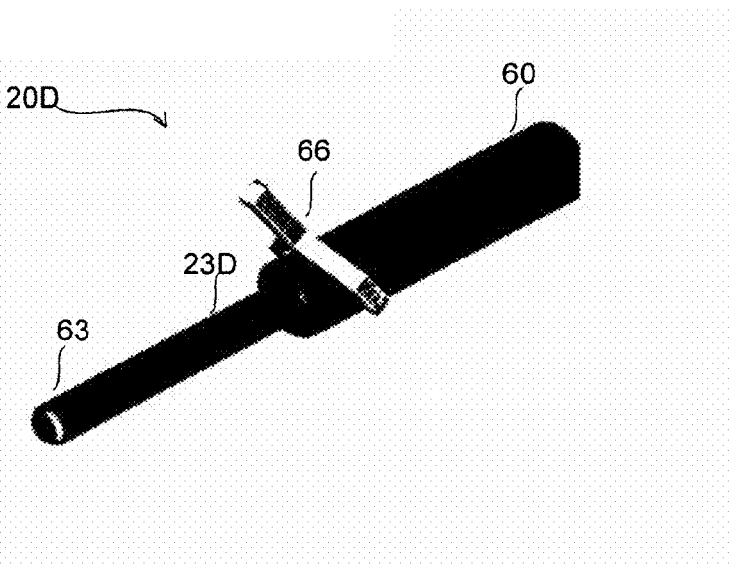

FIG. 3A, FIG. 3B, and FIG. 3C illustrate a stent mandrel fixture 20B in accordance with another embodiment of the invention. The stent mandrel fixture 20B is substantially similar to the stent mandrel fixture 20A except that the fixture 20B includes a substantially airtight inflatable cylinder or bladder 23B, which acts as a masking element to mask an inner surface of the stent 10 during a coating process, coupled to a pump 50 via a tube 52 in place of the tube 23A. As shown in FIG. 3C, which includes a cross section of the cylinder 23B, the cylinder 23B resembles a tire and comprises an outer diameter 54 and an inner diameter 56, and sidewalls which bound an interior airtight volume 55. The cylinder 23B includes a bore 57 formed by the inner diameter 56 through which the rod 24 travels.

The cylinder 23B can be fixed to the lock member 26 and/or nut 25, which act to prevent lateral movement of the cylinder 23B and stent 10 during a coating process. In addition, the lock member 26 and/or the nut 25 are rotationally mounted on the threaded rod 24, thereby enabling incremental positioning of the lock member 26 and the nut 25 with the cylinder 23B there between. In an alternative embodiment, the cylinder 23B is fixed to either the lock member 26 and/or the nut 25 and can act to seal the volume 55 if the cylinder 23B does not include sidewalls. In another embodiment of the invention, the diameter of the bore 57 is substantially equal to the outer diameter of the rod 24, thereby enabling a friction fit of the cylinder 23B onto the rod 24, which prevents unwanted lateral movement of the cylinder 23B during a coating process. Accordingly, the rod 24 need not be threaded and lock member 26 and nut 25 are not needed.

The interior volume 55 is in communication with the pump 50 via the tube 52. The pump 50 supplies gas or fluid to the interior volume 55 causing pressure to increase within the interior volume 55, thereby causing the outer diameter 54 to expand radially outwards from the rod 24, as shown in FIG. 5B. The supplied gas can have a temperature other than room temperature. The supplied gas, for example, can have a temperature between 35° C. and 80° C., to induce the evaporation of a solvent, preferably non-volatile solvents. Alternatively, the supplied gas can be cooler than 25° C. to retard the evaporation of the solvent, preferable retardation of the evaporation of unlike solvents.

In an embodiment of the invention, the inner diameter 56 is slightly larger than the diameter of the rod 24 while the outer diameter 54, in an unexpanded state, is less than the inner diameter of the stent 10, as positioned on the cylinder 23B. In one embodiment, the cylinder 23B has a length at least equal to the length of the stent 10, thereby enabling masking the entire length of the inner diameter of the stent 10. In another embodiment of the invention, the cylinder 23B is less than the length of the stent 10, thereby enabling masking of only a portion of the length of the inner diameter of the stent 10. The cylinder 23B is capable of expanding to at least the inner diameter of the stent 10 when the pump 50 pumps air into the interior area 55 of the cylinder 23B to increase the pressure within the cylinder 23B to, for example, 60-80 PSI. When the cylinder 23B is in an expanded state, the cylinder 23B acts to support the stent 10 and to mask the inner surface of the stent 10 (as shown in FIG. 5B) during a coating process so that the inner surface of the stent 10 is not coated with the same composition as the outer surface of the stent 10. In another embodiment of the invention, the sidewalls of the stent 10 can also be masked by the cylinder 23B as shown in FIG. 6A.

During operation of the stent mandrel fixture 20B, a stent 10 is loaded onto the fixture 20B by placing the stent 10 over the cylinder 23B when the cylinder 23B in an uncompressed state (FIG. 5A). The pump 50 then pumps gas into the interior area 55 of the cylinder 23B causing the outer diameter 54 of the cylinder 23B to expand radially outwards. In one embodiment of the invention, the cylinder 23B can expand radially outwards to substantially mask the inner surface of the stent 10, as shown in FIG. 5B. In another embodiment of the invention, the cylinder 23B can comprise a flexible and/or thin material, e.g., latex, and expands radially outwards to substantially mask the inner surface of the stent 10 as well as the sidewalls of the stent 10, as shown in FIG. 6A.

After the cylinder 23B is expanded radially outwards, a spray nozzle (not shown) sprays a composition onto the stent 10. As the inner diameter of the stent 10 is masked, only the sidewalls and outer diameter of the stent 10 are coated with a composition. In another embodiment of the invention, the sidewalls can also be masked and accordingly, only the outer surface of the stent 10 is coated with the composition.

After the coating of the stent 10, the pump 50 vents gas from within the interior volume 55, thereby lowering the pressure within the interior area 55 and enabling the tube 23B to return to a non-expanded state and further enabling removal of the stent 10 from the stent mandrel fixture 20B. The stent 10 can then have the inner surface coated via electroplating or spray coating.

FIG. 3D illustrates a stent mandrel fixture 20C in accordance with another embodiment of the invention. The fixture 20C, like the fixture 20B, is pneumatic-based. A cylinder 23C, for being placed through a bore of the stent 10, circumscribes a rod 24C. The cylinder 23C is an expandable tube having an inner volume constrained by the rod 24C. The rod 24C includes an inner bore and outlets 53 in fluid communication with the bore that feed gas, from the pump 50, into the interior volume of the cylinder 23C, thereby causing the cylinder 23C to expand radially outwards. The bore is in communication with a tube 59A, which is in communication with a coupling 58. The coupling 58 is in communication with the pump 50 via a tube 59B. Accordingly, gas from the pump 50 can travel through the tube 59B to and through the coupling 58 to and through the tube 59A to the rod 24C and through the outlets 53 into the interior volume of the cylinder 23C. The coupling 58 enables the rod 24C and cylinder 23C to rotate during a coating process without having to rotate the pump 50.

During a coating process, the pump 50 pumps air into the cylinder 23C thereby causing the cylinder 23C to expand to the inner diameter of the stent 10 (when the stent 10 is in an unexpanded state) thereby masking the inner diameter. In another embodiment of the invention, the cylinder 23C can expand past the inner diameter of the stent 10 to at least partially mask the sidewalls of the stent 10. After a coating process is complete, the pump 50 can vent gas from the interior region of the cylinder 23C, enabling it to return to its natural uncompressed state.

In an embodiment of the invention, the fixtures 20B and 20C can also include a pressure monitor disposed within the cylinder 23B or 23C. The pressure monitor can be coupled to feedback lines that provide the pump 50 with a measurement of pressure within the cylinder 23B or 23C so that the pump 50 can adjust the amount of gas pumped into the cylinder 23B or 23C.

FIG. 4A, FIG. 4B, FIG. 4C, and FIG. 4D illustrate a stent mandrel fixture 20D in accordance with another embodiment of the invention. The fixture 20D comprises a mandrel base 60 for receiving a rod 62; a tube or cylinder 23D that circumscribes the rod 62 and acts as a masking element to mask an inner surface of the stent 10 during a coating process; and a toggle switch 66 that is coupled to the rod 62, which acts as an expansion causing mechanism. In one embodiment of the invention, the mandrel base 60 is about 2 inches long with a diameter of about ⅜ of an inch and can be made of stainless steel.

The rod 62 has a disk 63 on the distal end. The rod 62 is coupled to the toggle switch 66 through a bore of the mandrel base 60 such that actuation of the switch 66 pulls the rod 62 further into the mandrel base 60, thereby pulling the disk 63 towards the mandrel base 60. The disk 63 laterally compresses the cylinder 23D against the mandrel base 60, thereby causing it to expand radially outwards. In one embodiment of the invention, the rod 62 is about 2.15 inches long with a diameter of about 0.28 inches and is made of stainless steel. The disk 63 of the rod 62 can also be made of stainless steel and have a diameter of about 0.55 inches with a width of 0.3 inches.

The cylinder 23D can be made of or coated with a non-stick material, such as TEFLON or low durometer PEBAX. The cylinder 23D circumscribes and is supported by the rod 62. The cylinder 23D is therefore constrained on both ends by the mandrel base 60 and the disk 63. Accordingly, when the cylinder 23D is compressed laterally between the mandrel base 60 and the disk 63, as is shown in FIG. 4B and FIG. 5B, the cylinder 23D is forced to expand outwards radially. In an embodiment of the invention, the cylinder 23D, in its uncompressed and unexpanded state, as shown in FIG. 4A and FIG. 5A, has an outer diameter of about 0.055 inches and an inner diameter of about 0.030 inches with a length of about 1.65 inches.

The toggle switch 66 changes the cylinder 23D between a compressed, expanded state and an uncompressed, non-expanded state. During operation of the stent mandrel fixture 20D, a stent 10 is loaded by placing it over cylinder 23D when the toggle switch 66 is placed in an open state as shown in FIG. 4A. The toggle switch 66 is then toggled to a closed or compressed state via an automated control or with human intervention as shown in FIG. 4B. The toggling of the toggle switch 66 pulls the rod 62 inwards towards the proximal end of the mandrel base 60, thereby pulling the disk 63 laterally inwards and compressing the cylinder 23D laterally, which causes the cylinder 23D to expand in a radial direction (i.e., the diameter of the cylinder 23D will increase) to mask the inner surface of the stent 10. The stent 10 can then be coated with a composition and dried while on the cylinder 23D. After application of the composition, the toggle switch 66 is moved to an open position, thereby decompressing the cylinder 23D so that the stent 10 can be released. As in all embodiments, the stent 10 can then be further dried in an oven until the solvent of the composition is evaporated.

Figure 5C:
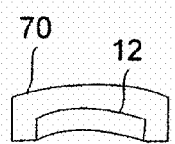
FIG. 5C illustrates a cross section of a stent strut after coating on the stent mandrel fixture of FIG. 2, FIG. 3, or FIG. 4.

FIGS. 5A and 5B illustrate cross sections of a stent mandrel fixture according to an embodiment of the invention. The stent mandrel fixture of FIG. 5A and FIG. 5B can include the embodiments shown in FIGS. 2A & 2B; FIG. 3A-3D; or FIG. 4A-4D. The stent mandrel fixture includes a masking element 23, such as the tube 23A or 23B, the masking element 23C, or the cylinder 23D having a bore within. The rod 24, 24C or rod 62 travels through the bore, thereby preventing the masking element 23 from expanding radially inwards when laterally compressed. When the masking element 23 is compressed laterally and expanded radially, as shown in FIG. 5B, the masking element 23 masks the inner surfaces 12C of the struts 12. Accordingly, during a coating process, only the exterior surface 12A and sidewalls 12B of the struts are coated with a composition leading to a coating 70 (FIG. 5C) on the exterior surface 12A and sidewalls 12B. A second coating (not shown) can be applied to the interior surfaces 12C via spraying, electroplating, or other conventional coating methods.

FIG. 6A illustrates a cross section of a stent mandrel fixture according to another embodiment of the invention. The stent mandrel fixture of FIG. 6A can include the embodiments shown in FIGS. 2A & 2B; FIG. 3A-3D; or FIG. 4A-4D. However, the masking element 23 is capable of partially or completely masking the sidewalls 12B in addition to the inner surfaces 12C. Accordingly, only the exterior surfaces 12A will be coated with a composition, forming a coating 72 (FIG. 6B), which can, for example, include a substantially pure drug composition. The masking element 23 can then be unexpanded to mask only the inner surfaces 12C as shown in FIG. 5B and a second coating applied, thereby forming coating 74 (FIG. 6C), which can include, for example, a substantially pure polymer. In an alternative embodiment, after applying the coating 72, the masking element 23 can be fully unexpanded, as shown in FIG. 5A, and then a coating applied, thereby encapsulating the coating 72 and all sides of the struts 12 with a coating 76 (FIG. 6D), which can include, for example, a substantially pure polymer. Advantages of the coatings applied as in FIGS. 6C and 6D include less coating on the stent 10 as only the exterior surfaces 12A are coated with a drug; encapsulation of the struts 12 prevents delamination or peeling at the edges of the struts 12; the encapsulating coating 74 or 76 can control drug release and have biocompatible properties; and drugs can be placed on the struts 12 where needed (e.g., a restenosis drug can placed solely on the exterior surfaces 12A, where it is needed), thereby preventing excessive use of the drug.

Figure 7:
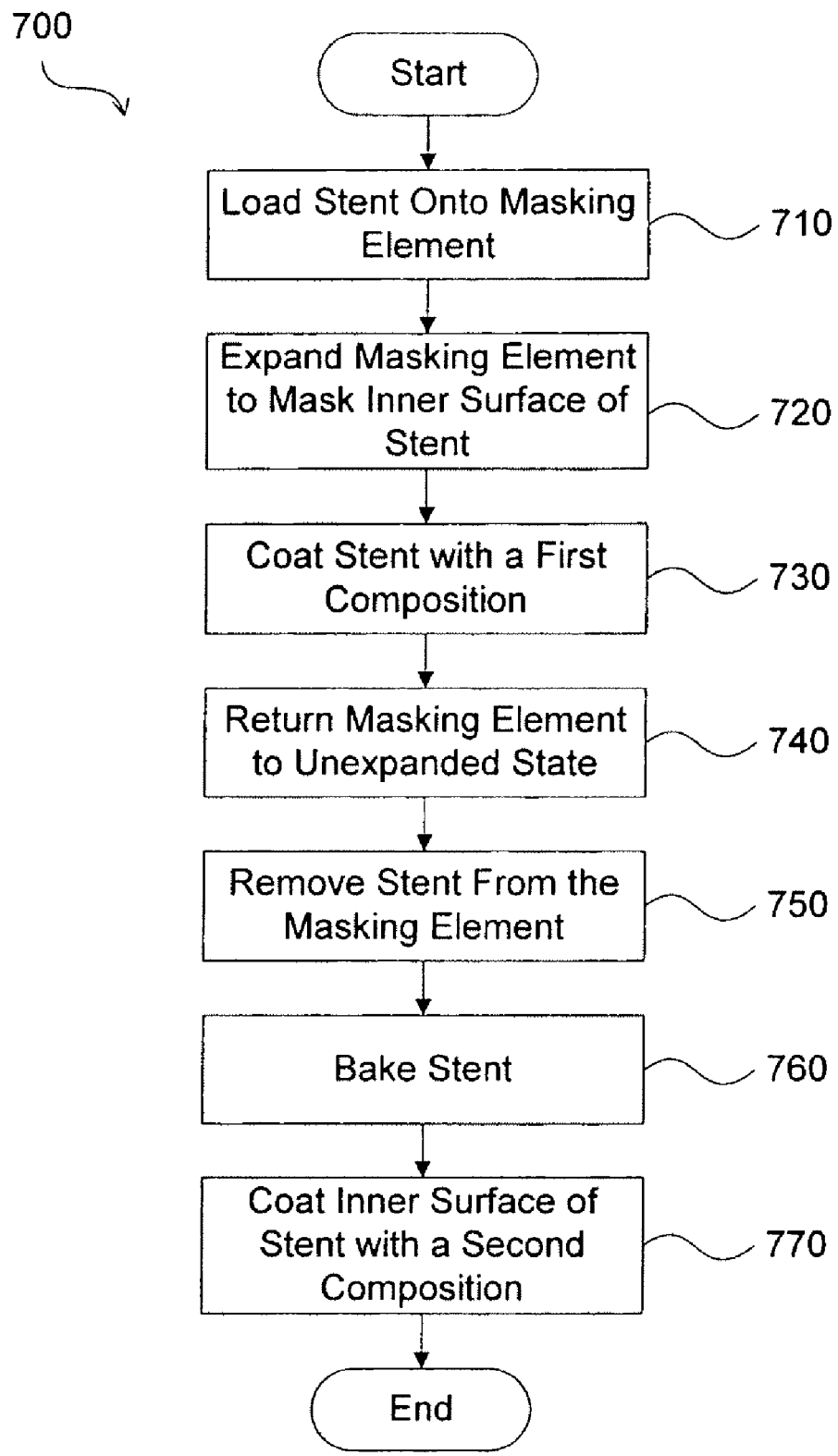
FIG. 7 illustrates a flowchart of a method of coating a stent using the stent mandrel fixture of FIG. 2, FIG. 3 or FIG. 4.

FIG. 7 illustrates a flowchart of a method 700 of coating a stent using the stent mandrel fixture 20A (FIG. 2A-FIG. 2B); 20B (FIG. 3A-FIG. 3D); or 20D (FIG. 4A-FIG. 4D). First, a stent 10 is loaded (710) over a masking element such as the tube 23A, or the cylinder 23B, 23C, or 23D (or other expandable masking element). The masking element is then expanded (720) until the masking element has an outer diameter at least equal to the inner diameter of the stent 10, thereby masking the inner surface of the stent 10. The expansion (720) can be invoked by an expansion causing mechanism such as the nut 25, the pump 50, or the toggle switch 66. In an alternative embodiment of the invention, the masking element can be further expanded to completely or partially cover the sidewalls in addition to the inner surface of the stent 10. The stent 10 is then coated (730) with a first composition. Due to the masking of at least the inner surface of the stent 10, only the outer surface and possibly the sidewalls (depending on how far the masking element is expanded) are coated (730) with the first composition. The masking element is then returned (740) to an unexpanded state and the stent 10 is removed (750) from the mandrel 24. The stent 10 is then baked (760) to remove solvent and so that the composition dries and hardens on the stent 10. The inner surface of the stent 10 is then coated (770), if desired, with a second composition having a therapeutic substance different from a therapeutic substance in the first composition. The coating (770) can be done via spraying or electroplating the composition. The method 700 then ends.

In another embodiment of the invention, in place of the removing (750) through the coating (770), the masking element can be unexpanded to less than the inner diameter of the stent 10 or up to the diameter of the stent 10 and then the stent 10 can be coated with a second composition (e.g., polymer) to encapsulate most or all of the surfaces of the stent 10. The stent 10 can then be removed from the masking element and baked to evaporate any solvent and to harden the coatings.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent support for partially covering a stent during an application of a coating composition, comprising:
   means for masking a luminal and side surface of a stent using a tube, so that only an outer surface of the stent is coated by a coating substance when pressure is applied to the sides of the tube by an expansion causing mechanism including a threaded rod that passes through a bore of the tube; and
   an engine connected to the means for masking and configured for rotating the stent during the application of the coating composition.

2. The stent support of claim 1, wherein the tube has a thin and/or flexible material capable of protruding at least partially through a gap between stent struts to mask sidewalls of stent struts.

3. The stent support of claim 2, wherein the thin and/or flexible material is polytetraflouroethylene.

4. The stent support of claim 2, wherein the thin and/or flexible material is capable of conforming to the shape of the stent strut so that the material masks the side and luminal surface of the stent strut.

5. The stent support of claim 1, wherein the pressure is applied by a nut received on the threaded rod.

6. The stent support of claim 1, wherein the expansion causing mechanism further includes a nut received on the threaded rod.

7. A stent support, comprising:
a masking element for inserting through a bore of a stent, the masking element having an expanded configuration and a retracted configuration; and
an expansion causing mechanism capable of expanding the masking element from the retracted configuration to the expanded configuration to cause the masking element to mask both an inner surface and a side surface of the stent, wherein the expansion causing mechanism comprises
a lock portion,
a nut, and
a rod having a threaded portion within the masking element and connecting the nut to the lock portion such that rotation of the nut on the threaded portion of the rod compresses the masking element in a lateral direction, the compression causing the masking element to mask both the luminal and side surface of a stent strut when the masking element is expanded.

8. The stent support of claim 7, wherein the masking element is capable of extending between stent struts without expanding the stent.

9. The stent support of claim 7, wherein the masking element is made of, or coated with a non-stick substance.

10. A stent support for stents that are to be partially coated with a coating composition, comprising:
a base;
a masking element;
a rod having a longitudinal axis and configured to be moved into or out of the base; and
a lever for placing the masking element on at least a luminal surface of a stent when the rod is at least moved parallel to its longitudinal axis and into the base including a coupling between the rod and the lever, wherein the coupling converts rotational motion of the lever about an axis perpendicular to the longitudinal axis to motion of the rod parallel to the longitudinal axis.

11. The stent support of claim 10, wherein the masking element is a thin and/or flexible material capable of protruding at least partially through a gap between stent struts to mask the sidewalls of the stent struts.

* * * * *